(12) United States Patent
Gifford

(10) Patent No.: US 9,683,927 B2
(45) Date of Patent: Jun. 20, 2017

(54) DEVICE FOR RECEIVING SMALL VOLUME LIQUID SAMPLES

(71) Applicant: Biochrom Limited, Cambridge (GB)

(72) Inventor: Graham Eric Gifford, Toft (GB)

(73) Assignee: Biochrom Limited, Cambridge (GB)

( * ) Notice: Subject to any disclaimer, the term of this patent is extended or adjusted under 35 U.S.C. 154(b) by 0 days.

(21) Appl. No.: 14/362,206

(22) PCT Filed: Nov. 8, 2012

(86) PCT No.: PCT/GB2012/052778
§ 371 (c)(1),
(2) Date: Jun. 2, 2014

(87) PCT Pub. No.: WO2013/079916
PCT Pub. Date: Jun. 6, 2013

(65) Prior Publication Data
US 2014/0356234 A1    Dec. 4, 2014

(30) Foreign Application Priority Data

Dec. 2, 2011  (GB) .................................. 1120769.3

(51) Int. Cl.
*G01N 21/01*   (2006.01)
*G01J 3/02*    (2006.01)
(Continued)

(52) U.S. Cl.
CPC ............ *G01N 21/0303* (2013.01); *G01J 3/02* (2013.01); *G01J 3/0218* (2013.01); *G01N 21/01* (2013.01);
(Continued)

(58) Field of Classification Search
None
See application file for complete search history.

(56) References Cited

U.S. PATENT DOCUMENTS

| 4,540,280 A | 9/1985 | Anderson et al. |
| 4,643,580 A | 2/1987 | Gross et al. |

(Continued)

FOREIGN PATENT DOCUMENTS

| EP | 0468019 | 1/1992 |
| EP | 0935749 B1 | 8/2002 |

(Continued)

OTHER PUBLICATIONS

English-language abstract of Japanese Patent No. JP 59 073753 A, European Patent Office, 1984.

(Continued)

*Primary Examiner* — Neil N Turk
(74) *Attorney, Agent, or Firm* — DASCENZO Intellectual Property Law, P.C.

(57) ABSTRACT

Improvements in and relating to devices for receiving liquid samples A device for receiving a liquid sample may form part of a micro sampling head for an instrument such as a spectrophotometer. The device receives a liquid sample to be analyzed by a process involving the passing of electromagnetic radiation through the sample, and comprises a light inlet guide (20) for directing electromagnetic radiation into the sample, a light receiving element (23) situated in an opposed relationship to the guide and spaced from the guide by a fixed distance to define a fixed path length gap (21), which is, in use, filled with the sample. In use, radiation is passed from the light inlet guide to the light receiving element (23), and the path length of radiation through the sample is defined by the gap (23). The device is open or openable to allow a droplet of sample to be deposited directly in the gap.

18 Claims, 5 Drawing Sheets

(51) Int. Cl.
  *G01N 21/31* (2006.01)
  *G01N 21/03* (2006.01)
(52) U.S. Cl.
  CPC .......... *G01N 2021/035* (2013.01); *G01N 2201/0846* (2013.01)

(56) References Cited

U.S. PATENT DOCUMENTS

| | | | |
|---|---|---|---|
| 5,428,696 | A | 6/1995 | Cahill et al. |
| 5,602,647 | A | 2/1997 | Xu et al. |
| 5,766,959 | A | 6/1998 | Dasgupta |
| 5,770,156 | A | 6/1998 | Dosoretz et al. |
| 6,204,919 | B1 | 3/2001 | Barshad et al. |
| 6,219,312 | B1 | 4/2001 | Hirata |
| 6,458,213 | B1 | 10/2002 | Krieg et al. |
| 6,764,654 | B2 | 7/2004 | Sasaki et al. |
| 6,831,746 | B2 | 12/2004 | Cassidy et al. |
| 6,835,350 | B2 | 12/2004 | Sasaki et al. |
| 6,914,680 | B2 | 7/2005 | Kawate |
| 7,061,619 | B2 | 6/2006 | Shirai et al. |
| 7,227,642 | B2 | 6/2007 | Oida et al. |
| 7,251,022 | B2 | 7/2007 | Martin et al. |
| 7,561,256 | B2 | 7/2009 | Neubert |
| 7,740,804 | B2 | 6/2010 | Samsoondar |
| 7,796,261 | B2 | 9/2010 | Juhl |
| 7,847,944 | B2 | 12/2010 | Buettner et al. |
| 2003/0059948 | A1 | 3/2003 | Hildenbrand et al. |
| 2005/0210996 | A1 | 9/2005 | Quinn et al. |
| 2007/0030482 | A1 | 2/2007 | Ji et al. |
| 2007/0182965 | A1 | 8/2007 | Kamlet et al. |
| 2008/0002927 | A1* | 1/2008 | Furnish ............ A61B 5/0075 385/12 |
| 2009/0086191 | A1 | 4/2009 | Bristol |
| 2010/0002981 | A1 | 1/2010 | Tang et al. |
| 2010/0277727 | A1 | 11/2010 | Schlaminger |
| 2011/0249265 | A1 | 10/2011 | Brenneman |

FOREIGN PATENT DOCUMENTS

| | | |
|---|---|---|
| EP | 1141675 B1 | 7/2005 |
| EP | 1704403 B1 | 9/2007 |
| EP | 1297320 B1 | 2/2008 |
| JP | 59 073753 A | 4/1984 |
| JP | 63 148144 A | 6/1988 |
| JP | H02 95842 U | 7/1990 |
| JP | 2008 116314 A | 5/2008 |
| WO | WO 96/14569 | 5/1996 |
| WO | WO 99/09455 | 2/1999 |
| WO | WO 01/14855 | 3/2001 |
| WO | WO 03/058212 | 7/2003 |
| WO | WO 2004/106872 | 12/2004 |
| WO | WO 2006/013832 | 2/2006 |
| WO | WO 2007/062800 | 6/2007 |
| WO | WO 2007/102783 | 9/2007 |
| WO | WO 2007/133757 | 11/2007 |
| WO | WO 2007/144583 | 12/2007 |
| WO | WO 2009/157057 | 12/2009 |
| WO | WO 2010/040104 | 4/2010 |
| WO | WO 2011/093775 | 8/2011 |

OTHER PUBLICATIONS

English-language abstract of Japanese Patent No. JP 63 148144, Japan Patent Office, 1988.
English-language abstract of European Patent No. 0468019, European Patent Office, Jan. 29, 1992.
English-language abstract of PCT Patent Application Publication No. WO 2003/058212, World Intellectual Property Organization, Jul. 17, 2003.
English-language abstract of PCT Patent Application Publication No. WO 2006/013832, World Intellectual Property Organization, Feb. 9, 2006.
English-language abstract of Japanese Patent No. JP 2008 116314 A, Japan Patent Office, 2008.
English-language abstract of PCT Patent Application Publication No. WO 2009/157057, World Intellectual Property Organization, Dec. 30, 2009.

* cited by examiner

DEVICE FOR RECEIVING SMALL VOLUME LIQUID SAMPLES

FIELD OF THE INVENTION

This invention relates to a device for receiving a liquid sample to be analysed by a process involving passing electromagnetic radiation through the sample, to a sampling head for apparatus for analysing such a sample photometrically or spectrophotometrically, and to a spectrophotometer having such a sampling head.

BACKGROUND TO THE INVENTION

The invention is of particular application to the analysis of low volume liquid samples, for example of volumes of 5 microliters or less, such as would be used in the quantitative analysis of aqueous samples of DNA created in the laboratory. Since is such a sample is a valuable resource, only a very small amount is generally available for assessment.

A common method of analysis of such a sample is by spectrophotometry, which involves passing a beam of electromagnetic radiation (for example ultraviolet light) through the sample and measuring the amount of light absorbed at different wavelengths (down to 200 nm).

WO01/14855 shows a liquid photometer in which surface tension is utilised to contain a sample in contact with a lower support surface which is situated opposite an upper support mounted on a swing arm. Such a device is mechanically relatively complex, and the relative moveability of the surfaces results in the requirement that the device needs periodic calibration in view of the possible variations in the length of the path light through the sample over the course of successive uses of the apparatus.

U.S. Pat. No. 4,540,280 shows a fibre optic thin layer cell for use in spectrophotometric analysis of a liquid. In this case, the light passes across a gap defined by the opposed ends of two bundles of optical fibres which are, in effect, cemented to the cell, and are therefore at a fixed position relative to each other. However, the liquid sample has to be fed into the cell through channels, and the cell interior is not readily accessible for cleaning after use.

JP63148144 shows a photometric device whereby the chemical analyser, comprising an optical fibre having a recessed core at one end to provide a volume into which a liquid sample may be placed, to be retained by the portion of the fibre cladding that stands proud of the core. In this case, light is conveyed to and from the sample through the surrounding cladding. Although the path light supplied through the sample is fixed, the volume into which the sample is to be placed can only be accessed through the relatively small tip of the fibre.

SUMMARY OF THE INVENTION

According to a first aspect of the invention, there is provided a device for receiving a liquid sample to be analysed by a process of involving the passing of electromagnetic radiation through the sample, the sample comprising a light inlet guide for directing electromagnetic radiation into the sample, a light receiving element, situated in an opposed relationship to the guide, and spaced from the guide by a fixed distance to define a fixed length gap which is, in use, filled with the sample and across which the radiation passes from the light inlet guide to the light receiving element, the path length of radiation through the sample being defined by said gap, the device being open or openable to allow a droplet of the sample to be deposited directly in the gap.

Such a device can be of a relatively simple, robust, construction which provides a fixed, accurately determinable path length for electromagnetic radiation through the sample, thus facilitating measurement conditions which are accurately determined and repeatable. Furthermore, since the inlet guide and light receiving element are spaced from each other, the gap is relatively accessible, for ease of introduction of liquid and subsequent cleaning.

Preferably, the light inlet guide is elongate, having an output end face through which, in use, electromagnetic radiation is emitted into said gap, and preferably the face constitutes one side of the gap, the light receiving element constituting the other side.

Preferably, the position of the face relative to the light receiving element is fixed.

Preferably, the light inlet guide comprises an inlet optical fibre.

Preferably, the axis of the fibre, at least at said face, intersects said element.

An optical fibre provides a convenient way of connecting in the device to a source of electromagnetic radiation, for example a light source such as a xenon lamp, that is not necessarily immediately adjacent to the device.

Preferably, at least the portion of the inlet fibre in the region of the output end is encased in a rigid cladding.

Since the end region of the fibre which terminates in the output end face will be sufficiently exposed to allow direct access to the gap, the rigid cladding provides useful protection which enables, for example, the surfaces defining the gap to be wiped clean without damaging, moving or deforming that portion of the fibre.

Preferably, the rigid cladding extends to the end of the fibre at which said face is situated.

Thus, where the end face of the fibre is planar, the rigid cladding may extend to the plane containing said face.

Preferably, the cladding is adhered or otherwise bonded to the fibre. This enables the cladding to be clamped or held so that the fibre is firmly held in position, thus facilitating a construction of device in which the size of the gap can be reliably maintained, over the course of multiple uses.

Preferably, the rigid cladding comprises a tube, preferably of metal or alloy, for example steel.

Preferably, the fibre has a core against which the tube directly bears.

The receiving elements may comprise a reflector for reflecting electromagnetic radiation from the output end face of the fibre to a further optical element, such as a detector for the radiation, or a further fibre for conveying said radiation to such a detector.

Preferably, however, the receiving element comprises a receiving end face of a further optical fibre, the two end faces thus defining the gap.

Preferably, the further fibre is of the same construction as the inlet fibre.

Preferably, the inlet fibre and the further fibre are co-axial, at least in the region of their receiving and output end faces.

Preferably, the fibres are, in use, horizontal, so that each of the end faces defines a respective side of the gap.

Preferably, the device has a housing having a recess into which the fibres extend, the gap being situated in the recess.

The recess facilitates access to the gap, whilst the housing provides some protection and positional fixing for the fibres.

In the latter case where the fibres have rigid claddings, the housing preferably engages the rigid claddings to hold the fibres in position relative to each other.

Preferably, the ends of both fibres stand proud of the recess.

Preferably, where the fibres have rigid cladding, the ends of the rigid claddings also stand proud of the recess.

Preferably, the fibres are the only optical fibres extending into the recess.

This further simplifies the construction of the device.

Preferably, the length of the gap between the end faces is such that a single 1 microliter drop of liquid will fill or flood the gap. To that end, the length of the gap is preferably 0.5 millimeters plus or minus 1%.

According to a second aspect of the invention, there is provided a micro-sampling head, comprising a device as aforesaid, for a spectrophotometer, photometer, fluorometer or spectrofluorometer.

The invention also lies in a spectrophotometer having such a sampling head.

BRIEF DESCRIPTION OF THE DRAWINGS

The invention will now be described by way of example only, with reference to the accompanying drawings in which.

DETAILED DESCRIPTION

Figure 1:
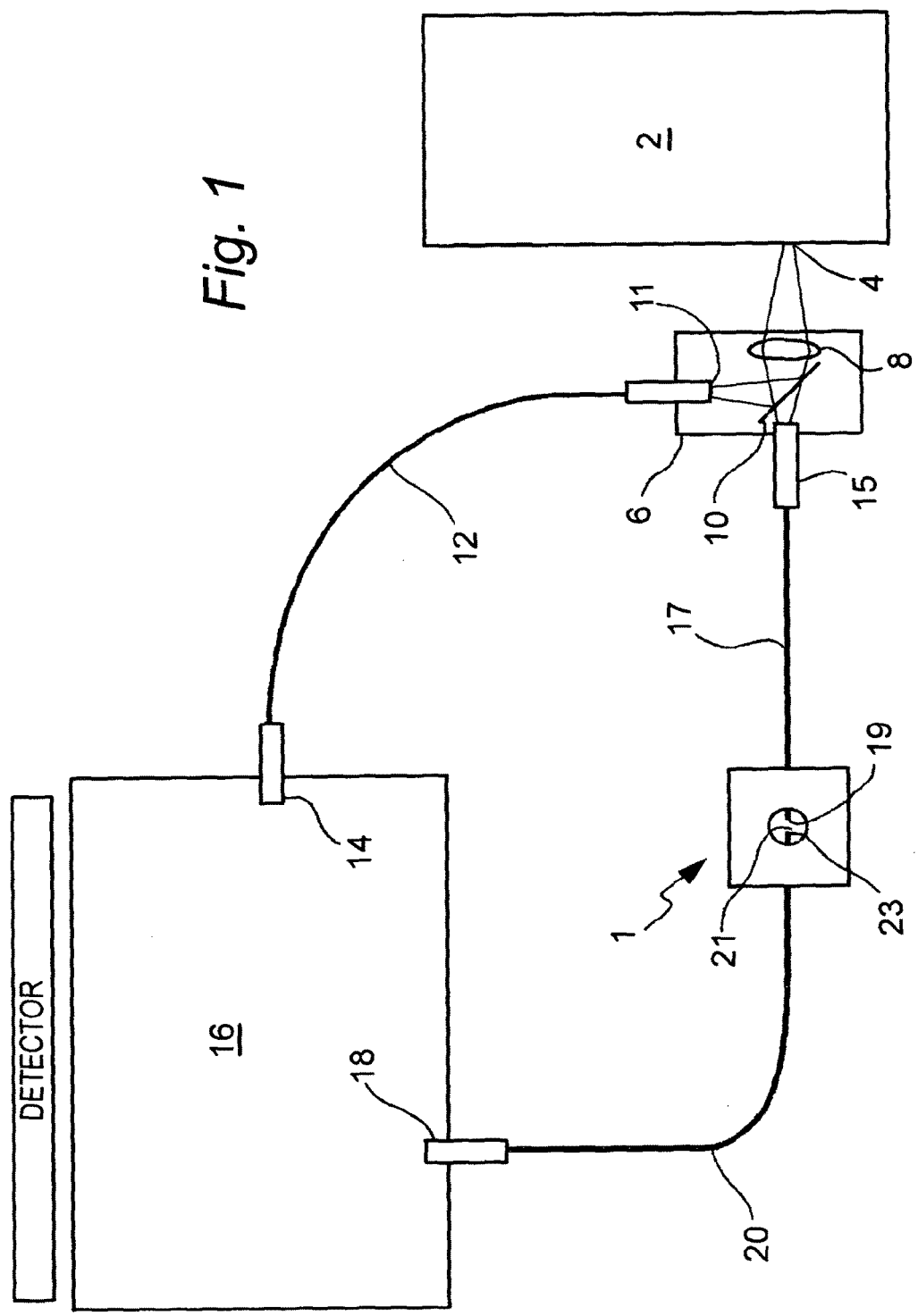
FIG. 1 is a schematic view of a spectrophotometer in accordance with the invention, the spectrophotometer having a sampling head also in accordance with the invention.

The spectrophotometer shown in FIG. 1 is for use in analysis liquid samples (containing DNA and other proteins) supplied to the analyser in droplets of a volume of around 1 to 2 microliters. Each droplet is, in turn, received in a device 1 for receiving a liquid sample, which is also in accordance with the invention, the device constituting part of a sampling head. The spectrophotometer is aimed at the DNA analysis market, and is designed to measure DNA concentrations in the range 2-2500 ng/μl. The remaining components of the spectrophotometer are the same as those for a conventional spectrophotometer, and include a xenon flash lamp source 2 operable to produce flashes of light in a range of wavelengths to extending from the UV to near IR (200 nm to 1100 nm).

The xenon flash lamp source 2 has an output 4, through which light is emitted to a beam splitter 6. The beam splitter 6 has an aperture through which that light passes to a condenser lens 8 for focussing light from the source 4 onto a half-silvered window 10. The half-silvered window 10 splits the incident light into two separate beams, one of which is incident on the inlet end 11 of a silica optical fibre 12, the outlet end 14 of which is connected to the reference channel input of a monochromator 16.

The monochromator 16 is of a known kind that converts incoming broadband light into individual or narrow bandwidth components, the intensity of each of which is measured by means of an appropriate detector (e.g. a CCD, a photodiode array, photomultiplier or single photo diode) forming part of the monochromator. The monochromator is of a type that can analyse light from two inputs to provide two sets of spectral data that can be compared. The splitting of the incoming light from each input may be achieved by any one of a number of possible means, such as interference filters, diffraction gratings or prisms. In this example, the monochromator uses diffraction gratings, and is constructionally and functionally substantially the same as the monochromator of the spectrophotometer described in WO2007/144583.

The output of the monochromator is fed to a display (not shown) and the operation of the monochromator can be controlled by means of suitable input controls (not shown).

The second beam from the beam splitter 6 is fed to the inlet end 15 of an inlet optical silica fibre 17 of the sampling head. The fibre 17 terminates at an end face 19 which constitutes one side of a gap 21. The other side of the gap 21 is constituted by a face 23 of a further optical fibre 20. The gap 21, in use, accommodates a sample to be is analysed, and the face 19 acts as an outlet end face for light being supplied to the gap 21 via the fibre 17. The Face 23 acts as an inlet face for the light emitted through the face 19 across gap 21.

The outlet end 18 of the further fibre 20 is connected to signal channel input of the monochromator 16. The construction of the sampling head 1 will now be described in more detail.

Figure 2:
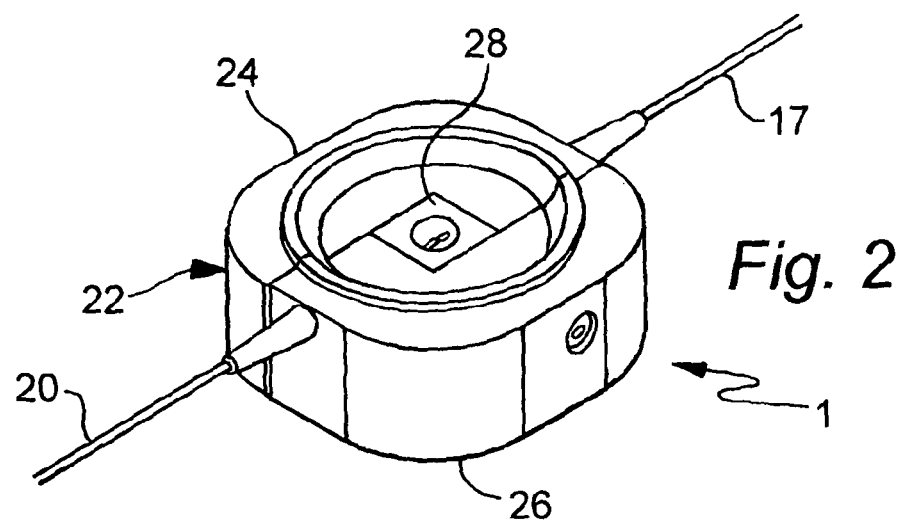
FIG. 2 is an isometric view of the sampling head.
Figure 3:
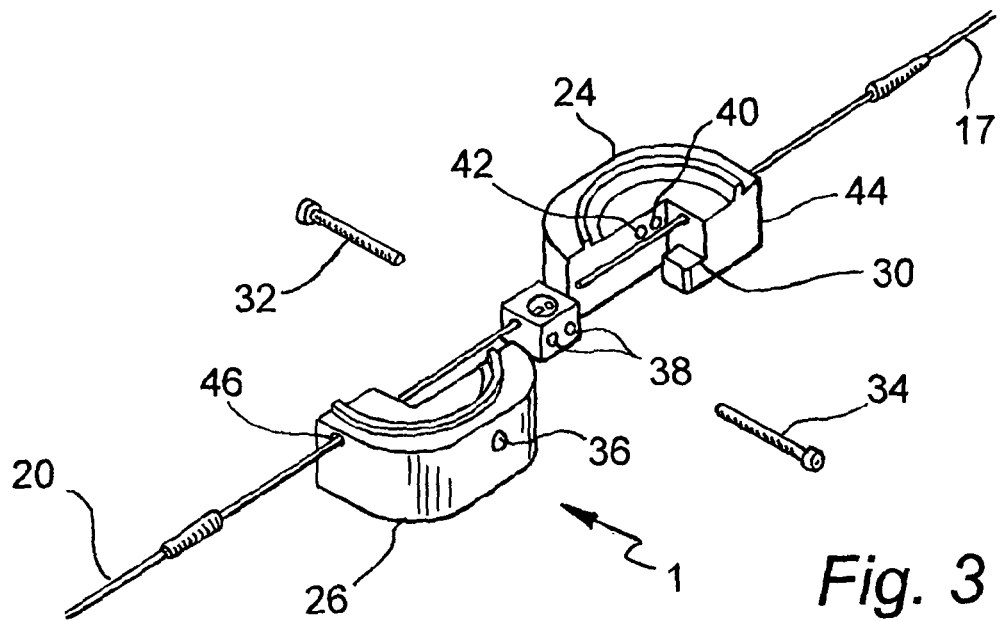
FIG. 3 is an exploded isometric view of the sampling head.

As can be seen from FIGS. 2 and 3, the sampling head 1 comprises a housing assembly 22 formed from a pair of complementary L-shaped clamping portions 24 and 26 which clamp a generally cubic central portion 28 of the housing 22 in place. Each clamping portion has an inner step, such as step 30 of portion 24, which defines a respective part of a square platform on which the portion 28 sits. The clamping portions and central cubic portion are all held together by means of screws 32 and 34, each of which passes through or into aligned screw threaded bores in each of the clamping portions 24 and 26 and the central portion 28. In FIG. 3, one of the bores in the portion 26 is shown at 36, and is a through bore. The portion 28 has a pair of parallel through bores referenced 38, and the clamping portion 24 has a blind bore 40 situated adjacent a through bore 42. The screw 34 passes through the through bore 36, one of the through bores 38 and into the blind bore 40, whilst the screw 32 passes through the through bore 42, through the other of the bores 38 and into a corresponding blind bore (not visible in FIG. 3) in the clamping portion.

The clamping portions 24 and 26 also have end through bores, respectively referenced 44 and 46 through each of which one of the respective fibres 17 and 20 extends to the central portion 28.

Figure 4:
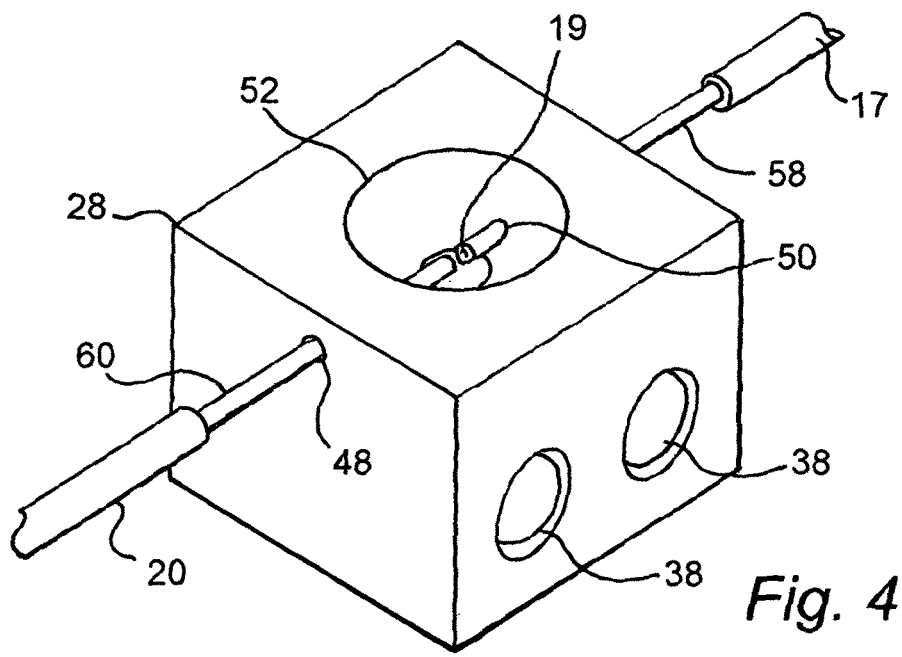
FIG. 4 is an isometric view of the central portion of the sampling head, having a housing and a recess in which a liquid sample is placed.
Figure 5:
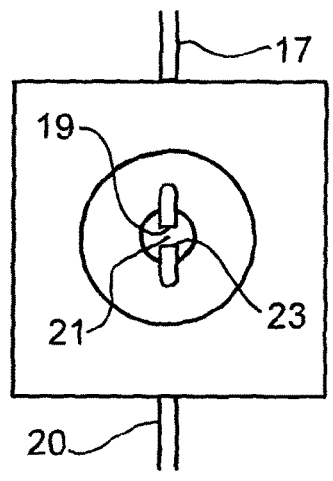
FIG. 5 is a plan view of the central portion.
Figure 6:
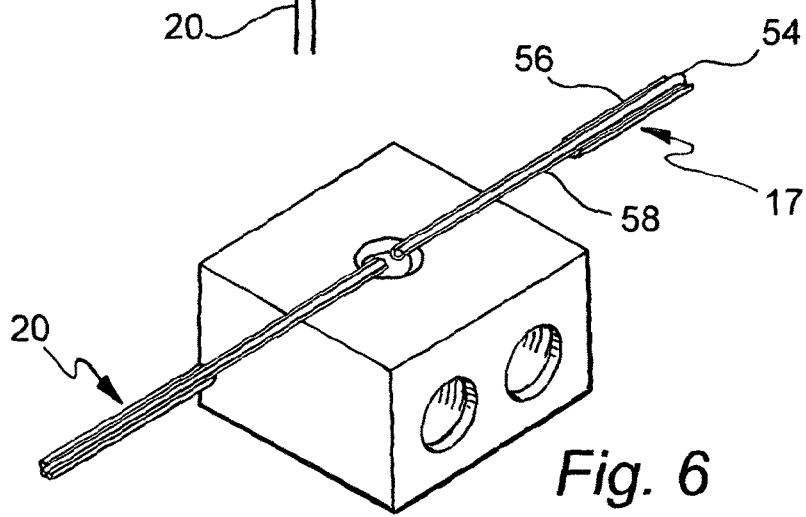
FIG. 6 is sectional isometric view of the central portion, the section being taken in a horizontal plane that contains the axes of inlet and outlet optical fibres forming part of the sampling head.

The central portion 28 is shown in more detail in FIGS. 4-6 and also includes a pair of opposed co-axial through bores 48 and 50 extending from a respective outer face of the portion 28 to a central, generally bowled recess 52.

The fibres 17 and 20 are of the same construction and so only the construction of the fibre 17 will be described in detail. The fibre 17 has over the majority of its length a central transparent, flexible core 54 of 220 μm diameter surrounded by flexible transparent cladding 56 having a lower index of refraction than the core so that light can be transmitted along the fibres by a process of total internal reflection. However, in the region of the portion 28, the cladding 56 has been stripped away from the fibre, and the core encased in a protective steel tube 58. The tube 58 has an internal diameter which provides a close tolerance fit for the optical fibre 17, and the core is bonded into the tube by using glues commonly used in the fibre optics industry. The part of the fibre 17 that has the steel tube 58 is the portion that extends through the through bore 50 and into the recess 52. The steel tube for the fibre 20 is denoted by the reference numeral 60. The outer diameter of the steel tubes also closely correspond to the diameter of the bores 50 and 48, so that the tubes are a close fit within the bores.

Figure 9:
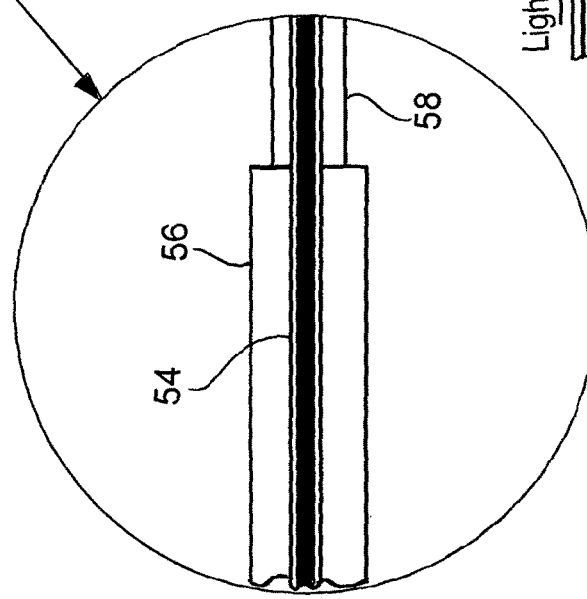
FIG. 9 is a more detailed view of part of the portion shown in FIG. 8.

The construction of the fibre 17 at the interface between the cladding 56 and the beginning of the steel tube 58 is shown in more detail in FIG. 9.

Figure 7:
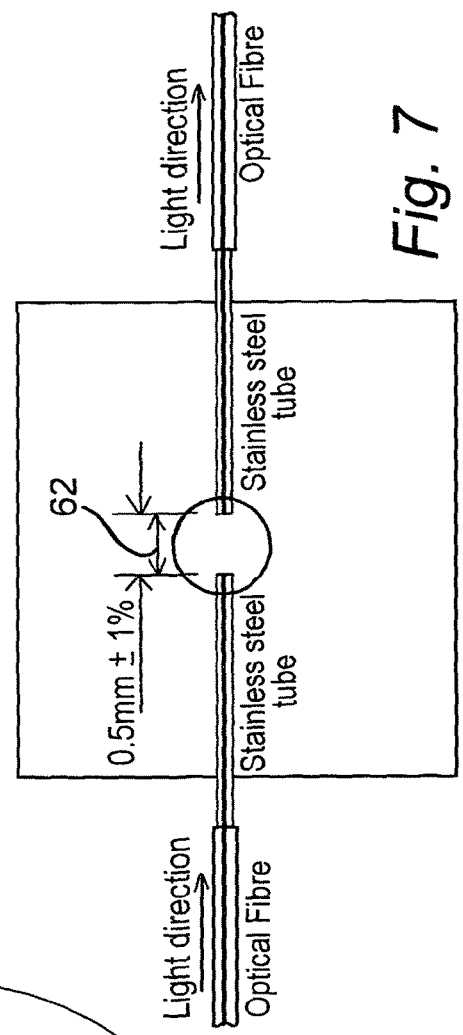
FIG. 7 is a sectional plan view of the central portion, the section being taken in the same plane as that of FIG. 6.
Figure 8:
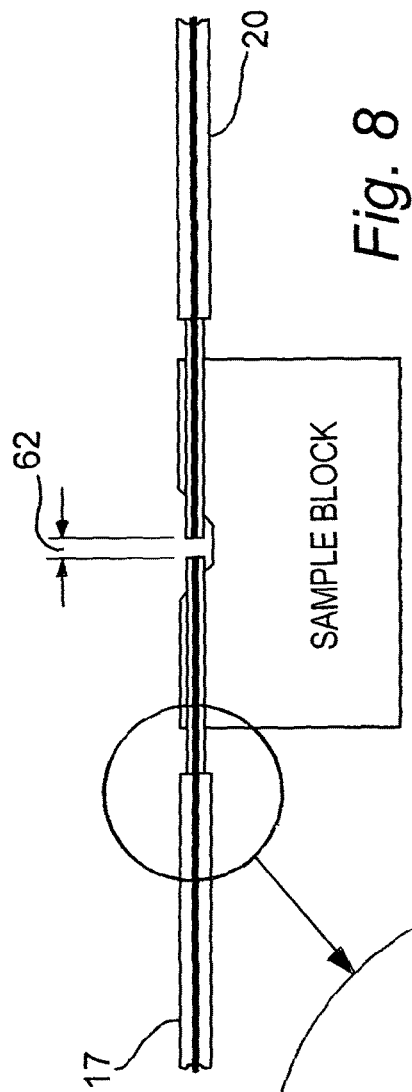
FIG. 8 is a sectional side view of the portion.

The fibres 17 and 20 are bonded (at their steel tubes) to the central portion 28. The surfaces of the end faces 19 and 23, the recess 52 and the portions of the tubes 58 and 60 which protrude into the recess 52 (so that the fibres stand proud of the recess) are coated with PTFE to assist in cleaning of the sampling head after a sample has been analysed. With reference to FIGS. 7 and 8, the tubes 58 and 60 are co-axial, and the gap 21 between their opposed end faces 19 and 23 has a length (i.e. distance in the direction 62) of 0.5 millimeters plus or minus 5 μm.

Figure 10:
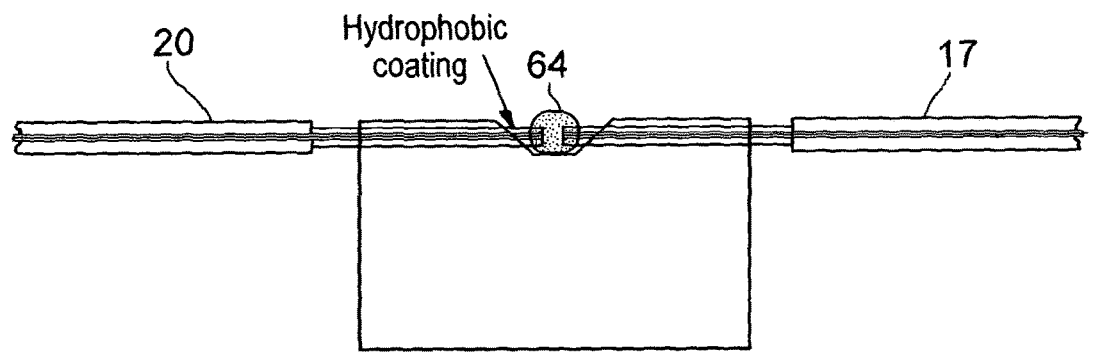
FIG. 10 is a view, corresponding to FIG. 8, showing a sample droplet in the portion of the sampling head.

In use, a droplet of 1 to 2 microliters, such as droplet 64 in FIG. 10 is deposited in the gap 21. As can be seen from FIG. 10, the droplet rests on the circular base on the recess 52 and extends to and around the tips of the fibres 17 and 20. The flash lamp source 2 then causes a train of light pulses to be supplied to the sampling head, in which the light then traverses the gap 21, which has been filled with the droplet 64, from the fibre 17 to the fibre 20 which conveys the transfer of light to the monochromator 16. A reference signal is simultaneously fed to the reference channel input of the monochromator 16 using the fibre 12. The light signals supplied to the two channels of the monochromator 16 are analysed in the conventional manner.

The sample 64 can be removed simply by wiping the surfaces within the recess 52 with a piece of tissue paper.

Although the cores of the fibres have only a very small diameter (200 micrometers in this case) the wiping action does not damage the fibres because of the protection provided by the tubes 58 and 60.

The components of the spectrophotometer, other than the sampling head 1 are contained within a housing (not shown). Since the sampling head 1 is connected to the rest of the system through flexible fibres, the spectrophotometer can be designed so that the head is situated outside or inside the housing. In the latter case, the housing will have an opening to allow access to the sampling head within.

The invention claimed is:

1. A device for receiving a liquid sample to be analysed by a process of involving the passing of electromagnetic radiation through the sample, the device comprising a housing assembly, a light inlet guide supported by the housing assembly for directing electromagnetic radiation into the sample, a light receiving element supported by the housing assembly, situated in an opposed relationship to the guide, and spaced from the guide by a fixed distance to define a fixed length gap for receiving, and being filled with, the sample, the device being operable to cause the radiation to pass from the light inlet guide to the light receiving element, the path length of radiation through the sample being defined by said gap, the housing assembly having a recess to allow a droplet of the sample to be deposited directly in the gap, wherein the gap is situated in the recess;

wherein the light inlet guide is elongate, having an output end face positioned within the recess and through which, in use, electromagnetic radiation is emitted into said gap;

wherein the light inlet guide comprises an inlet optical fibre including first and second regions, wherein the first region consists of a fibre core surrounded by a flexible cladding, and the second region consists of a rigid metallic cladding encasing the fibre core, and wherein the second region is located coincident with the output end face and adjacent to the gap.

2. The device according to claim 1, in which the output end face constitutes one side of the gap, the light receiving element constituting the other side.

3. The device according to claim 1, in which the position of the output end face relative to the light receiving element is fixed.

4. The device according to claim 1, in which the axis of the inlet optical fibre, at least at said output end face, intersects said light receiving element.

5. The device according to claim 1, in which the rigid metallic cladding extends to the end of the inlet optical fibre at which said output end face is situated.

6. The device according to claim 1, in which the rigid metallic cladding is bonded to the core of the inlet optical fibre.

7. The device according to claim 1, in which the rigid metallic cladding consists of a tube.

8. The device according to claim 7, in which the tube is a steel tube.

9. The device according to claim 8, in which the core directly bears against the steel tube.

10. The device according to claim 1, in which the light receiving element comprises a receiving end face of a further optical fibre, the output end face and the receiving end face thus defining the gap.

11. The device according to claim 10, in which the further optical fibre is of the same construction as the inlet optical fibre, said further optical fibre including third and fourth regions, wherein the third region consists of a further fibre core surrounded by a further flexible cladding, and the fourth region consists of a further rigid metallic cladding encasing the further fibre core, and wherein the fourth region is located coincident with the receiving end face and adjacent to the gap.

12. The device according to claim 11, in which the inlet optical fibre and the further optical fibre are co-axial, at least in the region of the receiving end face and the output end face.

13. The device according to claim 12, in which the coaxial portions of the inlet optical fibre and the further optical fibre are horizontal, so that each of the receiving end face and the output end face defines a respective side of the gap.

14. The device according to claim 11, in which the receiving end face and the output end face and the rigid metallic claddings of the inlet optical fibre and the further optical fibre stand proud of the recess.

15. The device according to claim 11, in which the inlet optical fibre and the further optical fibre are the only optical fibres extending into the recess.

16. The device according claim 10, in which the gap is so sized and positioned that a single 1 microliter drop of liquid will fill or flood the gap.

17. The device according to claim 16, in which the length of the gap is 0.5 millimeters plus or minus 1%.

18. A spectrophotometer comprising a device for receiving a liquid sample to be analysed by the spectrophotometer, the device comprising a housing assembly, a light inlet guide supported by the housing assembly for directing electromagnetic radiation into the sample, the light inlet guide having an inlet, and a light receiving element supported by the housing assembly, situated in an opposed relationship to the guide, and spaced from the guide by a fixed distance to define a fixed length gap for receiving, and being filled with, the sample, the spectrophotometer further comprising an electromagnetic radiation source for emitting electromagnetic radiation which is incident on an inlet end of the light inlet guide, the device being operable to cause the radiation to pass from the light inlet guide to the light receiving element, a path length of radiation through the sample being defined by said gap, the spectrophotometer further comprising a monochromator for analysing the radiation received by the light receiving element, wherein the housing assembly has a recess to allow a droplet of the sample to be deposited directly in the gap, wherein the gap is situated in the recess;

wherein the light inlet guide is elongate, having an output end face positioned within the recess and through which, in use, electromagnetic radiation is emitted into said gap;

wherein the light inlet guide comprises an inlet optical fibre including first and second regions, wherein the first region consists of a fibre core surrounded by a flexible cladding, and the second region consists of a rigid metallic cladding encasing the fibre core, and wherein the second region is located coincident with the output end face and adjacent to the gap.

* * * * *